United States Patent [19]

Prost

[11] 4,173,636
[45] Nov. 6, 1979

[54] DECAHYDROQUINOLINES, PHARMACEUTICAL COMPOSITIONS AND METHODS OF USE

[75] Inventor: Maurice Prost, Brussels, Belgium

[73] Assignee: Labaz, Paris, France

[21] Appl. No.: 884,705

[22] Filed: Mar. 8, 1978

Related U.S. Application Data

[63] Continuation of Ser. No. 745,542, Nov. 29, 1976, abandoned.

[30] Foreign Application Priority Data

Dec. 16, 1975 [GB] United Kingdom ............... 51507/75

[51] Int. Cl.² .................... A61K 31/47; C07D 215/44
[52] U.S. Cl. ................................. 424/258; 546/160; 546/161; 546/162
[58] Field of Search .................. 260/287 T; 424/258; 546/160, 162, 161

[56] References Cited
U.S. PATENT DOCUMENTS

| | | | |
|---|---|---|---|
| 3,455,929 | 7/1969 | Belleau et al. | 260/287 T |
| 3,882,129 | 5/1975 | Prost et al. | 260/287 T |

*Primary Examiner*—David Wheeler
*Attorney, Agent, or Firm*—Mason, Kolehmainen, Rathburn & Wyss

[57] ABSTRACT

The invention relates to decahydroquinoline derivatives represented by the general formula:

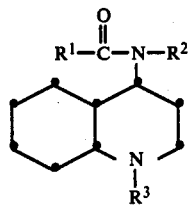

I and the pharmaceutically acceptable acid addition salts thereof, wherein $R^1$ represents an alkyl or alkoxy group, a lower dialkylamino group, an optionally substituted phenyl group, a heterocyclic group; $R^2$ represents an alkyl group, an optionally substituted phenyl group, a naphthyl group, an unsaturated heterocyclic group, an aralkyl group or an alicyclic group; and $R^3$ represents a substituted furyl group, an aralkyl group or a group represented by the general formula:

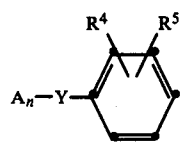

II wherein A represents an alkylene group; Y represents an oxygen or sulphur atom, a carbonyl, carbonyl-hydroxyimino, carbonyl-hydrazono or sulphoxide group, or a group;

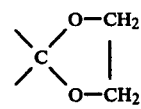

n is O or an integer of from 1 to 4, with the proviso that when n is O, Y represents a carbonyl group; and $R^4$ and $R^5$, which are identical or different, each represent hydrogen, a halogen atom or a methyl, methoxy or acetyl group.

Certain compounds of formula I have been found to possess useful analgesic properties while others have been found to be potentially useful in the treatment of high blood pressure.

14 Claims, No Drawings

DECAHYDROQUINOLINES, PHARMACEUTICAL COMPOSITIONS AND METHODS OF USE

This is a continuation of application Ser. No. 745,542 filed Nov. 29, 1976 now abandoned.

This invention relates to heterocyclic compounds and is concerned with 4-amino-trans-decahydroquinoline derivatives, with processes for preparing these derivatives and with pharmaceutical compositions containing them.

The compounds with which the present invention is concerned are those represented by the general formula:

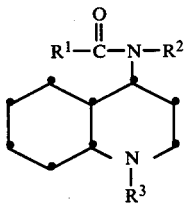

I and the pharmaceutically acceptable acid addition salts thereof, wherein $R^1$ represents a branched- or straight-chain alkyl or alkoxy group containing from 1 to 4 carbon atoms; a lower dialkylamino group such as dimethylamino; a saturated heterocyclic group such as pyrrolidino, piperidino or morpholino; an optionally substituted phenyl group; or an unsaturated heterocyclic group such as furyl or pyridyl; $R^2$ represents a branched- or straight-chain alkyl group containing from 1 to 4 carbon atoms; an optionally substituted phenyl group; a naphthyl group; an unsaturated heterocyclic group such as pyridyl, thienyl, methylthienyl, furyl or pyrimidyl; an aralkyl group such as benzyl, phenetyl, cinnamyl or phenylpropyl; or an alicyclic group such as cyclohexyl; and $R^3$ represents a lower alkyl substituted furyl group such as 2-methylfuryl; an aralkyl group such as benzyl, phenetyl, cinnamyl or phenylpropyl; or a group represented by the general formula:

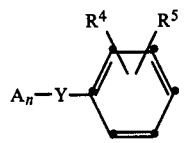

II wherein A represents a branched- or straight-chain alkylene group; Y represents an oxygen or sulphur atom, a carbonyl, carbonyl-hydroxyimino, carbonyl-hydrazono or sulphoxide group, or a group;

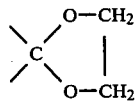

$R^4$ and $R^5$, which are identical or different, each represent hydrogen, a halogen atom, for example, fluorine, chlorine or bromine, or a methyl, methoxy or acetyl group; n is 0 or an integer of from 1 to 4, with the proviso that when n is 0, Y represents a carbonyl group.

The compounds of formula I in which $R^1$ represents an alkyl, an alkoxy or an optionally substituted phenyl radical, or an unsaturated heterocyclic group, may be prepared by refluxing a 1-substituted 4-amino-trans-decahydroquinoline having the general formula:

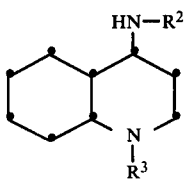

III wherein $R^2$ and $R^3$ have the same meanings as in formula I, preferably in an inert organic solvent such as, for example, dichloroethane, methylenechloride, benzene or toluene, with a compound of the general formula:

IV wherein $R^1$ has the meanings specified hereabove, optionally in the presence of a base such as, for example, triethylamine, trimethylamine or pyridine.

The compounds of formula I in which $R^1$ represents an alkyl, optionally substituted phenyl or unsaturated heterocyclic group may alternatively be prepared by refluxing a compound of general formula III, preferably in an inert organic solvent such as, for example, dichloroethane, methylenechloride, benzene or toluene, with a compound of the general formula:

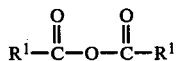

V wherein $R^1$ has the meanings specified hereabove, optionally in the presence of an acid such as, for example, p-toluene-sulphonic acid or sulphuric acid.

The compounds of formula I in which $R^1$ represents a lower dialkylamino group or a saturated heterocyclic group may be prepared by reacting a compound of formula III, preferably in an inert organic solvent such as, for example toluene, with phosgene, optionally in the presence of a base such as, for example, triethylamine or pyridine, to give a compound of the general formula:

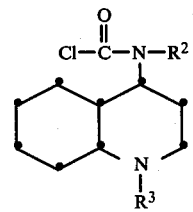

VI and thereafter reacting the compound of formula VI, preferably in an inert organic solvent such as, for example benzene, with an appropriate amine of the general formula:

VII wherein $R^1$ has the meanings specified hereabove.

The compounds of formula I can be converted into the corresponding pharmaceutically acceptable acid addition salt by treatment with an appropriate acid in accordance with techniques well known in the art.

The compounds of formula III may be prepared by reacting a 4-amino-trans-decahydroquinoline of the general formula:

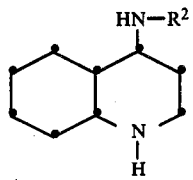

VIII wherein R² has the same meanings as in formula I, with a halogenated compound of the general formula:

Hal—R³     IX wherein Hal represents an atom of chlorine, bromine or iodine and R³ has the same meanings as in formula I. This reaction is preferably carried out in a liquid medium which may be an inert organic solvent such as, for example, benzene, toluene, xylene, dichloroethane or tetrahydrofuran, or an alcoholic medium, for example butanol or aqueous ethanol, or a ketone, for example acetone or methyl ethyl ketone, and in the presence of an acid acceptor, preferably an alkali metal carbonate, for example potassium carbonate or sodium bicarbonate.

The reaction, which may be accelerated by the use of small quantities of potassium iodide, is preferably carried out at the reflux temperature of the liquid medium.

The compounds of formula IX are already known while the compounds of formula VIII may be prepared by reacting the known compound 4-oxo-trans-decahydroquinoline, in the presence of a catalyst such as, for example, p-toluene-sulphonic acid, trifluoroboron etherate, zinc chloride or titanium tetrachloride, preferably in an inert organic solvent such as, for example, hexane, benzene or toluene and at the reflux temperature of the solvent, with an amine of the general formula:

R²—NH₂     X wherein R² has the same meanings as in formula I, the water formed being eliminated by azeotropic distillation. The imino derivative which is obtained is hydrogenated by means of sodium borohydride in methanol or lithium hydride in tetrahydrofuran. This hydrogenation may be carried out over a wide range of temperature.

The foregoing method produces the compounds of formula VIII in the form of a mixture of axial and equatorial isomers. This mixture may be separated into two fractions by virtue of differing solubilities of the hydrochloride of the isomers in an aqueous solution having a pH value of 3 or by chromatography. Hence the compounds of formulae I and III may be obtained either in the form of a mixture of their axial and equatorial isomers, or in the form of the axial or equatorial isomer. However it has not yet been possible to determine whether the fraction which is insoluble in water having a pH value of 3 is constituted by either the axial or equatorial isomer or possibly by a mixture of the two, and likewise with the soluble fraction. In view of this, the term "form a" will hereinafter be used to designate the compound represented by formula VIII of which the Rf in the chosen assay of thin-layer chromatography is smaller than that of the corresponding isomeric compound of formula VIII which will be designated hereinafter by the term "form b". The results of the thin-layer chromatographic assay in question are illustrated in the drawing accompanying this specification, details of the assay being as follows:

Support:
Silicagel 60 F.254 (produced by MERCK) thickness: 0.25 mm.
Development and saturation solvent (in ammonia atmosphere)
Hexane: 80 ml.
2-Propanol: 20 ml.
Technique: ascending 13 cm.
Deposits: 200 μg. (chloroform solution)
Revealing: U.V. at 2,540 Å in iodine vapour
(1) 4-phenylamino-trans-decahydroquinoline (form a)
(2) 4-phenylamino-trans-decahydroquinoline (form b)

The same denominations "form a" and "form b" will be used hereinafter to designate the corresponding isomers of the substances of formulae III and I of which the starting-product is either "form a" or "form b" of the compound represented by formula VIII. Consequently, the above-described process for obtaining the derivatives of formula I using derivatives of formula VIII as starting-products is equally applicable to either "form a" or "form b" of the derivatives of formula VIII for the preparation of the corresponding isomers of formula I.

The compounds of the invention have been found to possess valuable pharmacological properties and, in particular, some of them have been found to possess a powerful analgesic action which is devoid of any morphine-like effects.

Said properties render the compounds concerned of particular interest in the treatment of pain.

Thus the invention includes within its scope a method of relieving pain in a subject in need of such treatment by administering to the subject an effective amount of the appropriate compound of formula I or of a pharmaceutically acceptable acid addition salt thereof.

Analgesics are agents which relieve pain by acting centrally to elevate the pain threshold without disturbing consciousness or altering other sensory conditions.

Agents which are used principally for the symptomatic relief of pain may, for convenience of classification, be divided into two general groups:

(1) Narcotic analgesics, such as the opium derivatives.

Amongst these, morphine is one of the most important drugs and possesses numerous useful properties, analgesia being one of its main activities.

No other drugs is so generally useful in relieving various categories of severe pain. Unfortunately, morphine causes euphoria and addiction and it depresses respiration.

If morphine, or a related compound, is given over a long period of time, tolerance to the analgesic effect develops so that the dose must be increased periodically to obtain equivalent pain relief. For these reasons, it is generally agreed that morphine and its derivatives should not be used for pain when some other analgesic will suffice.

The analgesic compounds of the invention are completely devoid of any morphine-like effects and their use may therefore be recommended in a large number of cases than the morphine derivatives.

(2) Non-narcotic analgesics such as, for example, the salicylate derivatives.

These are generally less active than the narcotic analgesics but, on the other hand, they do not depress respiration and do not cause any or only very slight addiction.

It will be seen that the analgesic compounds of the invention compare very favourably to the most commonly used non-narcotic analgesics.

In addition to the above, some compounds of formula I have been found to possess useful pharmacological properties capable of rendering them of considerable value in the treatment of disorders of the cardiovascular system characterized by high blood pressure.

A further object of the invention is therefore a method of treating pathological disorders of arterial pressure and, in particular, hypertension in a subject in need of such treatment by administering to the said subject at least one appropriate compound of formula I or a pharmaceutically acceptable acid addition salt thereof.

The predominant types of hypertension are essential and malignant hypertension and there is no specific therapy for these diseases, individual cases varying widely as regards their response to various drugs.

They are therefore many antihypertensive agents which are used to treat the different types of hypertension.

Amongst them, some compounds are known to exert a ganglioplegic effect in that they interrupt the sympathicotonic impulses thus causing relaxation of the vascular walls. Others are characterized by a rather narrow margin between their therapeutic and toxic doses.

Finally, it is known that certain antihypertensive agents exert such a sudden and powerful antihypertensive effect that their action is difficult to control.

The antihypertensive compounds of the invention do not present these disadvantages.

Pharmacological tests have been undertaken with a view to demonstrating either the analgesic action or the antihypertensive effects of the compounds of the invention.

(1) Analgesic action

The following compounds of the invention were found to be particularly useful as analgesics:

4-[(N-phenyl-N-acetyl)-amino]-1-[3-(4-fluorobenzoyl)-propyl]-transdecahydroquinoline (Compound A).

4-[(N-phenyl-N-propionyl)-amino]-1-[3-(4-fluorobenzoyl)-propyl]-transdecahydroquinoline (Compound B).

4-[(N-phenyl-N-butyryl)-amino]-1-[3-(4-fluorobenzoyl)-propyl]-transdecahydroquinoline (Compound C).

4-[(N-phenyl-N-valeryl)-amino]-1-[3-(4-fluorobenzoyl)-propyl]-transdecahydroquinoline (Compound D).

4-[(N-4-methoxyphenyl-N-propionyl)-amino]-1-[3-(4-fluorobenzoyl)-propyl]-trans-decahydroquinoline (Compound E).

The first test was carried out according to the technique of KOSTER (Fed. Proc. 18, 412, 1959) on batches of 20 mice which had been deprived of food for 18 hours.

Each batch of animals with the exception of the controls was given an intragastric dose of the compound to be studied so that each batch received a higher dose than the preceding batch. Thirty minutes after administration, the animals of each batch, as well as the control animals, were given intraperitoneally 0.2 ml. of a 0.25% acetic acid solution per 10 g. of body-weight.

During the 20 minutes following the injection of acetic acid, the number of characteristic contorsions made by the animals was noted. The absence of contorsions corresponds to animals under the influence of analgesia.

Note was taken of the AD50, i.e. the dose of the compound under study which provoked analgesia in half of the animals treated.

The results of this test are given in the following Table:

TABLE I

| Compound | AD50 mg/kg |
| --- | --- |
| A | 38 |
| B | 25 |
| C | 30 |
| D | 25 |
| E | 55 |

The same test was carried out with five commonly used analgesics and the following results were obtained:

TABLE II

| Compound | AD50 mg/kg |
| --- | --- |
| Acetylsalicyclic acid | 150 |
| Antipyrine | 120 |
| Phenacetine | 160 |
| Glafenine | 110 |
| Pentazocine | 45 |

The second test was carried out according to the technique of NILSEN (Acta Pharmacol. et toxicol. 18, 10, 1961) on batches of 10 mice.

The animals were connected to a source of electric current by means of two electrodes inserted into the tail.

The threshold-voltage was then determined, i.e. the minimum voltage which, in the course of two successive shocks, caused the animals to squeak at least one time out of two. After this, the compound to be studied was administered by intragastric route. At various times after administration, four successive shocks were given at the threshold-voltage determined and it was considered that the animal was protected if it did not squeak after any of the shocks.

Note was taken of the dose of compound (AD50) which suppressed the squeak in half of the treated animals.

The results of this test are given in the following Table:

TABLE III

| Compound | AD50 mg/kg |
| --- | --- |
| A | 110 |
| B | 30 |
| C | 70 |

The same test was also carried out with three well-known analgesics and the following results were obtained:

TABLE IV

| Compound | AD50 mg/kg |
| --- | --- |
| Acetylsalicyclic acid | 1100 |
| Antipyrine | 400 |
| Phenacetine | 450 |

Further pharmacological tests were carried out with a view to determining the analgesic action of the preferred compound of the invention, namely: 4-[(N-phenyl-N-propionyl)-amino]-1-[3-(4-fluorobenzoyl)-propyl]-trans-decahydroquinoline (Compound B).

The first test was carried out according to the technique of KOSTER described above but using a sub-cutaneous injection of the product to be tested.

Compound B was compared to two major analgesics and the following results were obtained:

TABLE V

| Compound | AD50 mg/kg |
|---|---|
| B | 2 |
| Pethidine | 7 |
| Pentazocine | 5 |

The second test was carried out according to the technique of NILSEN described above but using a sub-cutaneous injection of the compound to be tested.

Compound B was compared to pethidine and pentazocine, two well-known analgesics, and the following results were obtained:

TABLE VI

| Compound | AD50 mg/kg |
|---|---|
| B | 4 |
| Pethidine | 7 |
| Pentazocine | 12 |

The third test was carried out according to the technique of SIEGMUND and al (Proc. Soc. Exp. Biol. Med. 95, 729, 1957) on batches of 10 male mice.

A typical syndrome was produced in the animals by intraperitoneal injection of 0.25 ml. of a 0.02% aqueous solution of 2-phenyl-1,4-benzoquinone (phenylbenzoquinone).

The syndrome in question is characterized by intermittent contractions of the abdomen, twisting and turning of the trunk and extension of the hind legs. Note was taken of the number of movements occurring over a period of 30 minutes starting 15 minutes after the injection of phenylbenzoquinone.

The compound to be tested was injected 30 minutes before the phenylbenzoquinone in such a way that each batch received a higher dose than the preceding batch, a control batch receiving only the phenylbenzoquinone.

Note was taken of the AD50, i.e. the dose of substance which reduced at least by half the number of contorsions in half of the animals, as compared to the number of contorsions observed in the control group.

The following results were obtained:

TABLE VII

| Compound | AD50 mg/kg |
|---|---|
| B | 7 |
| Acetylsalicyclic acid | 50 |
| Antipyrine | 100 |
| Phenacetine | 80 |
| Glafenine | 325 |

The fourth test was carried out according to the technique of CHARLIER and al (Arch. int. Pharmacodyn. 134, 306, 1961) on batches of 10 rats.

The animals were connected to a source of electric current by means of two electrodes of which one was attached to the tail and the other maintained in the rectum.

The pain-threshold voltage was then determined for each rat by passing a current of 2 volts and increasing the current by one volt at a time until the animal gave a squeak. This control test was repeated three times at intervals of 15 minutes. The compound under study was then administered by intragastric route and, starting from the threshold-voltage already determined note was taken, every 10 minutes for 2 hours, of the voltage which caused the animals to squeak.

The results were noted according to the WINTER and FLATAKER scale (J. Pharmacol. Exp. Therap. 98, 305, 1950) and the AD's 50 obtained are listed in the Table given hereunder:

TABLE VIII

| Compound | AD50 mg/kg |
|---|---|
| B | 30 |
| Acetylsalicylic acid | 1300 |
| Antipyrine | 500 |
| Phenacetine | 750 |
| Pethidine | 50 |

Finally, a test was carried out according to the technique of D'AMOUR and SMITH (J. Pharm. Exp. Ther. 72, 74, 1941) on batches of 10 male rats weighing about 200 g.

A 300-watt heating-bulb was focused on the tip of the rat's tail at such a distance that a typical twitch of the tail (flick-tail) was obtained after 4 to 6 seconds of irradiation.

The animals, with the exception of a control batch, were given the compound to be tested by sub-cutaneous route and note was taken of the time which elapsed between the beginning of irradiation and the first reaction of the animal (reaction time), as compared to the reaction time of the control animals.

The AD's 50 obtained are given in the following Table:

TABLE IX

| Compound | AD50 mg/kg |
|---|---|
| B | 2.5 |
| Pethidine | 5.5 |
| Pentazocine | 3 |

From the above tests, it may be concluded that the compounds of the invention possess analgesic properties which are far superior to those of well-known analgesics.

(2) Antihypertensive action

The compound of formula I wherein $R^1$ represents a branched- or straight-chain alkoxy group have been found to possess a useful antihypertensive action capable of rendering them of considerable value in the treatment of human hypertension.

As far as the treatment of hypertension is concerned, the preferred compound of the invention is:

4-[(N-phenyl-N-carbethoxy)-amino]-1-[3-(4-fluorobenzoyl)-propyl]-trans-decahydroquinoline (Compound F).

A pharmacological test was undertaken with a view to demonstrating the antihypertensive action of Compound F.

This test was carried out on male rats belonging to a race which has been specially bred to produce animals having high blood pressure, according to the technique of OKAMOTO and AOKI (Jap. Circul. J. 27, 282, 1963).

The animals employed were about ten weeks old and had a blood pressure reading in the region of 180 mm.Hg.

This test was divided into two series. In the first series, one single dose of the compound under study was administered by intragastric route to each animal and the arterial pressure of the latter was measured every hour for six hours after administration. In the second series, the product under study was given by the same route every day for eleven consecutive days and arterial pressure was measured daily throughout this period.

The amount of compound administered varied from one animal to another, as far as the first series of tests was concerned.

The following results were obtained:

TABLE X

| Type of treatment | Dose mg/kg | Max. fall in A.P. (mm.Hg) | Moment of max fall in A.P. |
|---|---|---|---|
| Single Dose | 5 | 27 | 3 hours |
| | 10 | 44 | 4 hours |
| Daily dose (eleven days) | 10 | 29 | 8 days |

From these results, it may be concluded that Compound F has a powerful antihypertensive action.

(3) Acute toxicity

Acute toxicity trials were carried out on rats and mice which were kept under observation for 12 days following one single administration.

The following results were obtained:

(a) Compound B

| Animals | Administration | LD50 (mg/kg) |
|---|---|---|
| Mice | intragastric | 500 |
| Rats | intragastric | 350 |
| Mice | intraperitoneal | 55 |
| Rats | intraperitoneal | 55 |
| Mice | sub-cutaneous | 550 |

(b) Compound F

| Animals | Administration | LD50 (mg/kg) |
|---|---|---|
| Mice | intragastric | 750 |
| Rats | intragastric | 450 |
| Rats | intravenous | 15 |
| Mice | intravenous | 32 |

These figures compare very favourably with the active doses of which the effects are described above and show that there is a very wide safety margin between the toxic doses and the therapeutic doses of the preferred compounds of the invention.

It will be appreciated that, for therapeutic use, the compounds of the invention will normally be administered in the form of a pharmaceutical composition containing as active principle at least one compound of formula I or a pharmaceutically acceptable acid addition salt thereof in association with a pharmaceutical carrier and/or excipient therefor.

Advantageously, for clinical use the composition will be made up in a dosage unit form appropriate to the desired mode of administration, for example a coated or uncoated tablet or a hard- or soft gelatin capsule for oral administration, a solution for injection or a suppository for rectal administration.

Irrespective of the form which the composition takes, the pharmaceutical composition will normally comprise at least one of the compounds of formula I or a pharmaceutically acceptable acid addition salt thereof associated with an appropriate pharmaceutical diluent or excipient comprising, for example, one or more of the following substances: milk, sugar, starches, talc, magnesium stearate, polyvinylpyrrolidone, alginic acid, colloidal silica or flavouring agent.

The following Examples illustrate the invention.

EXAMPLE 1

4-[(N-phenyl-N-propionyl)-amino]-1-[3-(4-fluorobenzoyl)-propyl]trans-decahydroquinoline hydrochloride (form a)

(a) Preparation of 4-phenylamino-trans-decahydroquinoline

A solution of 76.8 g. (0.5 mol) of 4-oxo-trans-decahydroquinoline and 1.0 g. of p-toluenesulphonic acid in 350 ml. of hexane was refluxed in a one-liter flask and 46.3 g. (0.5 mol) of aniline were added.

Refluxing was continued until the water which formed was completely eliminated by means of a Dean-Stark system and 140 ml. of hexane was distilled off. The solution was allowed to cool and 250 ml. of benzene were added. The reaction medium was firstly washed with water, then with a diluted solution of sodium hydroxide and finally again with water. The resulting solution was dried over anhydrous sodium sulphate, filtered and the solvents were eliminated to give 102.4 g. of crude 4-phenylimino-trans-decahydroquinoline (yield: 89%).

In a one-liter flask were dissolved the 102.4 g. of 4-phenylimino-trans-decahydroquinoline so obtained in 190 ml. of methanol containing 200 mg. of sodium hydroxide, the temperature of the solution being maintained at about 20° C.

A solution of 20 g. of sodium borohydride in 200 ml. of methanol, stabilized by 600 mg. of sodium hydroxide, was added following which the temperature of the reaction medium was maintained between 20 and 22° C. for a few hours.

The solution was finally heated to 40° C. for 8 hours and was then allowed to cool. The solvent was eliminated and the residue taken up in 150 ml. of benzene and 250 ml. of water.

The mixture was decanted and the aqueous phase was extracted with benzene. The organic phase was then extracted with 240 ml. of 4 N hydrochloric acid. The mixture was decanted and sodium hydroxide was added until a pH of 3 was obtained. Filtration was effected to obtain an aqueous acid filtrate and a precipitate which was dried so as to give 43.8 g. of 4-phenylamino-trans-decahydroquinoline hydrochloride (form a).

Yield: 33%, m.p. 265°–270° C.

Isolation of form b

The aqueous acid filtrate was made alkaline by adding sodium hydroxide and was extracted with benzene. The resulting mixture was decanted and the organic phase was washed with water, dried over anhydrous sodium sulphate and filtered. The benzene was eliminated and the residue taken up in 35 ml. of diethyl ether. The solution so formed was cooled to a temperature between 0° and 5° C., filtered and washed with diethyl ether to give 9.2 g. of 4-phenylamino-trans-decahydroquinoline (form b).

Yield: 7%, m.p. 118°–120° C.

By following the same method but using the appropriate starting-products, the compounds listed hereunder were prepared:

| Compound | Melting Point °C. |
| --- | --- |
| 4-(4-methylphenyl)-amino-trans-decahydroquinoline | 92–94 |
| 4-(4-methoxyphenyl)-amino-trans-decahydroquinoline | 144–145 |
| 4-benzylamino-trans-decahydroquinoline | uncristallized |
| 4-(1-naphthyl)-amino-trans-decahydroquinoline | uncristallized |
| 4-Cyclohexylamino-trans-decahydroquinoline | uncristallized |

(b) Preparation of 1-[(3-(fluorobenzoyl)-propyl]-4-phenyl-amino-trans-decahydroquinoline dihydrochloride (form a)

In a four-liter flask was refluxed a solution of 230 g. (1 mol) of 4-phenylamino-trans-decahydroquinoline (form a) in 920 ml. of n-butanol, in the presence of 100 g. of sodium bicarbonate. While refluxing, a solution of 274 g. (1.12 mols) of 3-chloro-1,1-ethylenedioxy-1-(4-fluoro-phenyl)-butane in 200 ml. of n-butanol was added and the reflux was maintained until the water which formed was completely eliminated by means of a Dean-Stark system. The solution was allowed to cool to 50° C. and the salts so formed were filtered off.

The solvent was eliminated under vacuum from the solution and the resulting residue was taken up in 2,500 ml. of benzene. The resulting solution was extracted with a solution of 250 ml. of concentrated hydrochloric acid in 1,250 ml. of water. The mixture obtained was decanted and the hydrochloric solution was stirred for 3 hours, made alkaline and then extracted with benzene. The organic phase obtained was washed with water, dried over anhydrous sodium sulphate and filtered and the benzene was eliminated. The residue obtained was taken up in ethyl acetate and a solution of gaseous hydrochloric acid in 2-propanol was added. The precipitate which formed was filtered off, washed with ethyl acetate and dried. The crude product obtained was recrystallized from a mixture of ethyl acetate and methanol and 303 g. of 1-[3-(4-fluorobenzoyl)-propyl]-4-phenylamino-trans-decahydroquinoline dihydrochloride were obtained (form a).

Yield: 64.8%, m.p. 204°–206° C.

By following the same method but using the appropriate starting-products, the compounds listed hereunder were prepared and their melting points obtained after recrystallization from the indicated solvents:

| Compound | Melting Point °C. |
| --- | --- |
| 1-[3-(4-fluorobenzoyl)-propyl]-4-(4-methoxyphenyl)-amino-trans-decahydroquinoline dihydrochloride (form a) | 179–182 (ethyl acetate/methanol) |
| 1-[3-(4-fluorobenzoyl)-propyl]-4-(4-methylphenyl)-amino-trans-decahydroquinoline dihydrochloride (form a) | 188–194 (ethyl acetate/methanol) |
| 1-(3-benzoylpropyl)-4-phenylamino-trans-decahydroquinoline hydrochloride (form a) | 206–208 (ethanol) |
| 1-[3-(4-methylbenzoyl)-propyl]-4-phenylamino-trans-decahydroquinoline hydrochloride (form a) | 226–227 (ethyl acetate/methanol) |
| 1-[3-(4-chlorobenzoyl)-propyl]-4-phenylamino-trans-decahydroquinoline hydrochloride (form a) | 248–249 (methanol, ethanol) |
| 1-[3-(4-fluorobenzoyl)-propyl]-4-phenylamino-trans-decahydroquinoline dihydrochloride (form b) | 227–230 (ethyl acetate/methanol) |
| 1-[3-(4-fluorobenzoyl)-propyl]-4-(4-methylphenyl)-amino-trans-decahydroquinoline dihydrochloride (form b) | 235–238 (ethyl acetate/methanol) |
| 1-[3-(4-bromobenzoyl)-propyl]-4-phenylamino-trans-decahydroquinoline hydrochloride (form a) | 241–243 (ethanol/methanol) |
| 1-[3-(4-methoxybenzoyl)-propyl]-4-phenylamino-trans-decahydroquinoline hydrochloride (form a) | 230–232 (ethanol) |
| 1-(4-fluorobenzoyl-methyl)-4-phenylamino-trans-decahydroquinoline hydrochloride (form a) | 255–257 (2-propanol) |
| 1-Benzomethyl-4-phenylamino-trans-decahydroquinoline hydrochloride (form a) | ±230 (decomposition) (ethanol/methanol) |
| 1-[3-(2-Thenoyl)-propyl]-4-phenylamino-trans-decahydroquinoline dihydrochloride (form a) | 167–169 (ethyl acetate/methanol) |
| 1-Phenethyl-4-phenylamino-trans-decahydroquinoline hydrochloride (form a) | 258–260 (ethanol) |
| 1-Cinnamyl-4-phenylamino-trans-decahydroquinoline acid oxalate trans-decahydroquinoline a) | 170–172 (2-propanol) |
| 1-(3-phenyl-propyl)-4-phenylamino-trans-decahydroquinoline oxalate (form a) | 148–150 (2-propanol) |
| 1-[3-(4-chlorobenzoyl)-propyl]-4-[(4-methoxyphenyl)-amino]-trans-decahydroquinoline dihydrochloride (form a) | 224–226 (ethyl acetate/methanol) |
| 1-[4-(4-fluorobenzoyl)-butyl]-4-phenylamino-trans-decahydroquinoline hydrochloride (form a) | 182–184 (ethanol) |
| 1-(2-Phenoxy-ethyl)-4-phenylamino-trans-decahydroquinoline (form a) | 165–167 (methanol) |
| 1-[3-(4-Fluoro-phenylthio)-propyl]-4-phenylamino-trans-decahydroquinoline (form a) | 83–85 (heptane) |
| 1-[3-(4-fluorobenzoyl)-propyl]-4-benzylamino-trans-decahydroquinoline hydrochloride (form a) | 255–256 (ethyl acetate/methanol) |
| 1-[3-(4-fluorobenzoyl)-propyl]-4-cyclohexylamino-trans-decahydroquinoline hydrochloride (form a) | 211–214 (ethyl acetate/methanol) |
| 1-[3-(4-fluorobenzoyl)-propyl]-4-(1-naphthylamino)-trans-decahydroquinoline | uncrystallized |

(c) Preparation of 4-[(N-phenyl-N-propionyl)-amino]-1-[3-(4-fluorobenzoyl)-propyl]-trans-decahydroquinoline hydrochloride While stirring, 394 g. (1 mol) of 1-[3-(4-fluorobenzoyl)-propyl]-4-phenylamino-trans-decahydroquinoline (form a) were dissolved in 800 ml. of dichloroethane in a two-liter flask. The resulting solution was cooled to about 20° C. and a solution of 105 ml. of propionyl chloride in 105 ml. of dichloroethane was added.

The reaction medium was then maintained at 20° C. for one hour after which it was heated to 45°–50° C. for 16 hours. The solution was thereafter cooled to 10°–15° C. and the resulting precipitate of 1-[3-(4-fluorobenzoyl)-propyl]-4-phenylamino-trans-decahydroquinoline dihydrochloride was filtered off.

The excess of propionyl chloride was hydrolysed with 120 ml. of methanol and the solution was evaporated to dryness.

The residue obtained was taken up in 150 ml. of acetone, refluxed and the solvent distilled off. This operation was repeated twice more.

At the reflux temperature of the solvent, the residue was dissolved in 150 ml. of acetone and a solution of 2-propanol containing a small quantity of gaseous hydrochloric acid was added. The resulting solution was allowed to crystallize at room-temperature and the precipitate obtained was filtered off, washed with acetone and dried to give 318 g. of crude product. After recrystallization from a mixture of ethyl acetate/methanol (2:1 by volume), 263 g. of 4-[(N-phenyl-N-propionyl)-amino]-1-[3-(4-fluorobenzoyl)-propyl]-trans-decahydroquinoline hydrochloride (form a) were obtained.

Yield: 54%, m.p. 158°-160° C.

By following the same method but using the appropriate staring-products, the compounds listed hereunder were prepared and their melting points obtained after recrystallization from the indicated solvents:

| Compound | Melting Point °C. |
|---|---|
| 4-[(N-phenyl-N-acetyl)-amino]-1-[3-(4-fluorobenzoyl)-propyl]-trans-decahydroquinoline hydrochloride (form a) | 168–170 (ethyl acetate/methanol) |
| 4-[(N-phenyl-N-butyryl)-amino]-1-[3-(4-fluorobenzoyl)-propyl]-trans-decahydroquinoline hydrochloride (form a) | 174–175 (ethyl acetate/methanol) |
| 4-[(N-phenyl-N-valeryl)-amino]-1-[3-(4-fluorobenzoyl)-propyl]-trans-decahydroquinoline hydrochloride (form a) | 158–160 (ethyl acetate/methanol) |
| 4-[(N-phenyl-N-propionyl)-amino]-1-[3-(4-fluorobenzoyl)-propyl]-trans-decahydroquinoline oxalate (form b) | 161–162 (ethyl acetate/acetone) |
| 4-[(N-4-methylphenyl-N-propionyl)-amino]-1-[3-(4-fluorobenzoyl)-propyl]-trans-decahydroquinoline hydrochloride (form a) | 201–203 (ethyl acetate/methanol) |
| 4-[(N-4-methoxyphenyl-N-propionyl)-amino]-1-[3-(4-fluorobenzoyl)-propyl]-trans-decahydroquinoline hydrochloride (form a) | 193–195 (ethyl acetate/methanol) |
| 4-[(N-phenyl-N-acetyl)-amino]-1-(3-benzoylpropyl)-trans-decahydroquinoline hydrochloride (form a) | 227–228 (ethyl acetate/methanol) |
| 4-[(N-phenyl-N-propionyl)-amino]-1-(3-benzoyl-propyl)-trans-decahydroquinoline hydrochloride (form a) | 128–130 (ethyl acetate/methanol) |
| 4-[(N-phenyl-N-acetyl)-amino]-1-[3-(4-methylbenzoyl)-propyl]-trans-decahydroquinoline hydrochoride (form a) | 185–186 (ethyl acetate/methanol) |
| 4-[(N-phenyl-N-propionyl)-amino]-1-[3-(4-methylbenzoyl)-propyl]-trans-decahydroquinoline hydrochloride (form a) | 214–215 (ethyl acetate/methanol) |
| 4-[(N-phenyl-N-acetyl)-amino]-1-[3-(4-chlorobenzoyl)-propyl]-trans-decahydroquinoline hydrochloride (form a) | 193–194 (ethyl acetate/methanol) |
| 4-[(N-phenyl-N-propionyl)-amino]-1-[3-(4-chlorobenzoyl)-propyl]-trans-decahydroquinoline hydrochloride (form a) | 130–131 (ethyl acetate/methanol) |
| 4-[(N-acetyl-N-phenyl)-amino]-1-[3-(4-fluorobenzoyl)-propyl]-trans-decahydroquinoline hydrochloride (form b) | 188–190 (ethyl acetate/methanol) |
| 4-[(N-benzoyl-N-phenyl)-amino]-1-[3-(4-fluorobenzoyl)-propyl]-trans-decahydroquinoline hydrochloride (form a) | 139–141 (ethyl acetate/hexane) |
| 4-[(N-Nicotinoyl-N-phenyl)-amino]-1-[3-(4-fluorobenzoyl)-propyl]-trans-decahydroquinoline dihydrochloride (form a) | 211–213 (methyl ethyl cetone/hexane) |
| 4-[(N-Isonicotinoyl-N-phenyl)-amino]-1-[3-(4-fluorobenzoyl)-propyl]-trans-decahydroquinoline dihydrochloride (form a) | 213–215 (methyl ethyl cetone/hexane) |
| 4-[(N-2-Furoyl-N-phenyl)-amino]-1-[3-(4-fluorobenzoyl)-propyl]-trans-decahydroquinoline hydrochloride (form a) | 230–231 (ethyl acetate/methanol) |
| 4-[(N-Acetyl-N-phenyl)-amino]-1-[3-(4-bromobenzoyl)-propyl]-trans-decahydroquinoline hydrochloride (form a) | 219–221 (ethyl acetate/methanol) |
| 4-[(N-Phenyl-N-propionyl)-amino]-1-[3-(4-bromobenzoyl)-propyl]-trans-decahydroquinoline hydrochloride (form a) | 143–145 (ethyl acetate/methanol) |
| 4-[(N-Acetyl-N-phenyl)-amino]-1-[3-(4-methoxybenzoyl)-propyl]-trans-decahydroquinoline hydrochloride (form a) | 184–186 (ethyl acetate/methanol) |
| 4-[(N-Phenyl-N-propionyl)-amino]-1-[3-(4-methoxybenzoyl)-propyl]-trans-decahydroquinoline hydrochloride (form a) | 214–216 (ethyl acetate/methanol) |
| 4-[(N-Acetyl-N-phenyl)-amino]-1-(4-fluorobenzoyl-methyl)-trans-decahydroquinoline hydrochloride (form a) | 236 (acetone) |
| 4-[(N-Phenyl-N-propionyl)-amino]-1-(4-fluorobenzoyl-methyl)-trans-decahydroquinoline hydrochloride (form a) | 225–227 (ethyl acetate/methanol) |
| 4-[(N-Acetyl-N-phenyl)-amino]-1-benzoylmethyl-trans-decahydroquinoline hydrochloride (form a) | 233–235 (ethyl acetate/methanol) |
| 4-[(N-Phenyl-N-propionyl)-amino]-1-benzoylmethyl-trans-decahydroquinoline hydrochloride (form a) | 229 (ethyl acetate/methanol) |
| 4-[(N-Acetyl-N-phenyl)-amino]-1-[3-(4-thenoyl)-propyl]-trans-decahydroquinoline hydrochloride (form a) | 205–207 (ethyl acetate/methanol) |
| 4-[(N-Phenyl-N-propionyl)-amino]-1-[3-(2-thenoyl)-propyl]-trans-decahydroquinoline hydrochloride (form a) | 111–113 (acetone) |
| 4-[(N-Acetyl N-4-methoxyphenyl)-amino]-1-[3-(4-chlorobenzoyl)-propyl]-trans-decahydroquinoline hydrochloride (form a) | 193–195 (ethyl acetate/methanol) |
| 4-[(N-4-Methoxyphenyl-N-propionyl)-amino]-1-[3-(4-chlorobenzoyl)-propyl]-trans-decahydroquinoline hydrochloride (form a) | 213–215 (acetone) |
| 4-[(N-Acetyl-N-phenyl)-amino]-1-[4-(4-fluorobenzoyl)-butyl]-trans-decahydroquinoline hydrochloride (form a) | 212–214 (acetone) |
| 4-[(N-Phenyl-N-propionyl)-amino]-1-[4-(4-fluorobenzoyl)-butyl]-trans-decahydroquinoline hydrochloride (form a) | 162–164 (ethyl acetate) |
| 4-[(N-Acetyl-N-phenyl)-amino]-1-benzyl-trans-decahydroquinoline hydrochloride (form a) | 180–182 (ethyl acetate) |
| 4-[(N-Phenyl-N-propionyl)-amino]-1-benzyl-trans-decahydroquinoline hydrochloride (form a) | 198–200 (ethyl acetate/methanol) |
| 4-[(N-Acetyl-N-phenyl)-amino]-1-phenethyl-trans-decahydroquinoline hydrochloride (form a) | 232–234 (ethyl acetate/methanol) |
| 4-[(N-Phenyl-N-propionyl)-amino]-1-phenethyl-trans-decahydroquinoline | 231–233 |

-continued

| Compound | Melting Point °C. |
|---|---|
| hydrochloride (form a) | (ethyl acetate/methanol) |
| 4-[(N-Acetyl-N-phenyl)-amino]-1-(3-phenylpropyl)-trans-decahydroquinoline hydrochloride (form a) | 196–198 (ethyl acetate/methanol) |
| 4-[(N-Phenyl-N-propionyl)-amino]-1-(3-phenylpropyl)-trans-decahydroquinoline hydrochloride (form a) | 210–212 (ethyl acetate/methanol) |
| 4-[(N-Acetyl-N-phenyl-amino]-1-cinnamyl-trans-decahydroquinoline (form a) | 136–138 (heptane) |
| 4-[(N-Benzyl-N-propionyl)-amino]-1-[3-(4-fluorobenzoyl)-propyl]-trans-decahydroquinoline hydrochloride (form a) | 147–149 (ethyl acetate/ diethyl ether) |
| 4-[(N-1-Naphthyl-N-propionyl)-amino]-1-[3-(4-fluorobenzoyl)-propyl]-trans-decahydroquinoline hydrochloride (form b) | 122–124 (ethyl acetate/methanol) |
| 4-[(N-Cyclohexyl-N-propionyl)-amino]-1-[3-(4-fluorobenzoyl)-propyl]-trans-decahydroquinoline hydrochloride (form a) | 154–156 (ethyl acetate/methanol) |
| 4-[(N-Cyclohexyl-N-propionyl)-amino]-1-[3-(4-fluorobenzoyl)-propyl]-trans-decahydroquinoline acid oxalate (form b) | 178–180 (ethyl acetate/methanol) |
| 4-[(N-Phenyl-N-acetyl)-amino]-1-[3-(4-fluorobenzoyl)-propyl]-trans-decahydroquinoline hydrochloride (form a) | 158–160 (ethyl acetate/methanol) |
| 4-[(N-Phenyl-N-propionyl)-amino]-1-(2-phenoxy-ethyl)-trans-decahydroquinoline hydrochloride (form a) | 159–161 (ethyl acetate/methanol) |
| 4-[(N-Phenyl-N-propionyl)-amino]-1-[3-(4-fluoro-phenylthio)-propyl]-trans-decahydroquinoline hydrochloride (form a) | 120–122 (ethyl acetate/methanol) |
| 4-[(N-Acetyl-N-phenyl)-amino]-1-[3-(4-fluoro-phenylthio)-propyl]-trans-decahydroquinoline hydrochloride (form a) | 150–152 (ethyl acetate/methanol) |

EXAMPLE 2

4-[(N-Phenyl-N-propionyl)-amino]-1-[3-(4-fluorobenzoyl)-propyl]-trans-decahydroquinoline hydrochloride (form a)

3.94 g. (0,085 mol) of 1-[(4-fluorobenzoyl)-propyl]-4-phenylamino-trans-decahydroquinoline hydrochloride (form a), prepared as in Example 1 were dissolved in 20 ml. of dimethylformamide and 3.5 ml. of propionylchloride were added to the solution.

The mixture was heated to 60°–80° C. for 40 hours and 5 ml. of methanol were added.

The reaction medium was distilled at 80° C. under vacuum until 12 ml. of the solution had distilled and the residue was poured into diluted sodium hydroxide. The reaction medium was extracted with diethyl ether and the organic solution was washed with water and treated with active charcoal. The solvent was eliminated end the residue was dissolved in 150 ml. of acetone at the reflux temperature of the solvent. A solution of 2-propanol containing a small quantity of gaseous hydrochloric acid was added and the resulting solution was allowed to crystallize at room-temperature. The precipitate obtained was filtered off, washed with acetone and dried to give 318 g. of crude product. After recrystallization from a mixture of ethyl acetate/methanol (2:1 by volume), 263 g. of 4-[(N-phenyl-N-propionyl)-amino]-1-[3-(4-fluorobenzoyl)-propyl]-trans-decahydroquinoline hydrochloride (form a) were obtained.

Yield: 65.1%, m.p. 158°–160° C.

EXAMPLE 3

4-[(N-Phenyl-N-propionyl)-amino]-1-[3-(4-fluorobenzoyl)-propyl]-trans-decahydroquinoline hydrochloride (form a)

A solution containing 6 g. (0.015 mol) of 1-[3-(4-fluorobenzoyl)propyl]-4-phenylamino-trans-decahydroquinoline (form a), prepared as in Example 1, 45 ml. of propionic anhydride and a trace of p-toluenesulphonic acid was heated to 100° C. for 20 hours. After cooling methanol was added and the same method as described in Example 1 (c) was followed to give 4.5 g. of 4-[(N-phenyl)-N-propionyl]-amino-1-[3-(4-fluorobenzoyl)-propyl]-trans-decahydroquinoline hydrochloride (form a).

Yield: 61.6%, m.p. 158°–160° C.

EXAMPLE 4

4-[(N-Phenyl-N-propionyl)-amino]-1-[3-(4-fluorobenzoyl)-propyl]-trans-decahydroquinoline methanesulfonate (form a)

A solution of benzene containing 98 g. (0.22 mol) of 4-[(N-phenyl-N-propionyl)-amino]-1-[3-(4-fluorobenzoyl)-propyl]-trans-decahydroquinoline (form a), prepared as in Example 1, was acidified by 30 g. of a 69.5% aqueous solution of methanesulfonic acid containing 2-propanol, until a pH of 3.5–4 was obtained.

The acid solution was evaporated to dryness and taken up in 600 ml. of toluene. By azeotropic distillation 100 ml. of toluene was eliminated and, after crystallization and filtration, 104 g. of 4-[(N-phenyl-N-propionyl)-amino]-1-[3-(4-fluorobenzoyl)-propyl]-trans-decahydroquinoline methanesulfonate (form a) were obtained.

Yield: 88%, m.p.: 132°–134° C.

EXAMPLE 5

4-[(N-Phenyl-N-propionyl)-amino]-1-[4-(4-fluorophenyl)-4-hydrazonobutyl]-trans-decahydroquinoline (form a)

A solution containing 2.5 ml. of hydrazine hydrate in 15 ml. of ethanol was mixed with 3.6 g. (0.008 mol) of 4-[(N-phenyl-N-propionyl)-amino]-1-[3-(4-fluorobenzoyl)-propy]-trans-decahydroquinoline (form a) and the mixture was refluxed for 3 hours. The solution was concentrated and the residue was poured into 100 ml. of water. The precipitate which formed was filtered off, washed with water and dried.

The substance was recrystallized from 2-propanol to give 4-[(N-phenyl-N-propionyl)-amino]-1-[4-(4-fluorophenyl)-4-hydrazonobutyl]-trans-decahydroquinoline (form a).

Yield: 84%, m.p.: 155°–156° C.

EXAMPLE 6

4-[(N-Phenyl-N-propionyl)-amino]-1-[4-(4-fluorophenyl)-4-hydroxyiminobutyl]-trans-decahydroquinoline (form a)

5 g. (0.011 mol) of 4-[(N-phenyl-N-propionyl)-amino]-1-[3-(4-fluorobenzoyl)-propyl]-trans-decahydroquinoline, prepared as in Example 1, were dissolved in 100 ml. of ethanol and a solution of 3.5 g. of hydroxylamine hydrochloride in 25 ml. of water and 7 g. of sodium hydrogenocarbonate were added. The reaction medium was refluxed for 12 hours and was concentrated under vacuum. The residue was poured into water and the precipitate which formed was filtered off, washed with water and dried. Recrystallization from 2-propanol gave 2.5 g. of 4-[N-phenyl-N-propionyl)-amino]-1-[4-(4-fluorophenyl-4-hydroxyimino-butyl]-trans-decahydroquinoline (form a).

Yield: 48%, m.p.: about 80° C.

EXAMPLE 7

55 g. (0.14 mol) of 1-[3-(4-fluorobenzoyl)-propyl]-4-phenylamino-trans-decahydroquinoline, prepared as in Example 1, were dissolved in 200 ml. of dichloroethane. While stirring, 16 g. of ethyl chloroformiate were added drop-by-drop and the medium was heated to 50°–60° C. for 16 hours. The reaction medium was cooled to 20° C. and a solution of gaseous hydrochloric acid in 2-propanol was added. Stirring was continued for between 2 and 3 minutes, the mixture was evaporated to dryness and the residue was taken up in acetone. The reaction medium was cooled to 0° C. for 16 hours and the excess of 1-[3-(4-fluorobenzoyl)-propyl]-4-phenylamino-trans-decahydroquinoline was removed by filtration. The filtrate was evaporated to dryness and the residue was taken up in ethyl acetate.

The organic solution was cooled to 0° C. for 16 hours and 4-[(N-carbethoxy-N-phenyl)-amino]-1-[3-(4-fluorobenzoyl)-propyl]-trans-decahydroquinoline hydrochloride (form a) crystallized and was filtered off and recrystallized from ethyl acetate/methanol.

Yield: 31%, m.p.: 134°–136° C.

By following the same method but using the appropriate starting-products, the compounds listed hereunder were prepared:

| Compound | Melting Point °C. |
|---|---|
| 4-[(N-carbophenoxy-N-phenyl)-amino]-1-[3-(4-fluorobenzoyl)-propyl]-trans-decahydroquinoline hydrochloride (form a) | 185–187 (ethyl acetate) |
| 4-[(N-carbomethoxy-N-phenyl)-amino]-1-[3-(4-fluorobenzoyl)-propyl]-trans-decahydroquinoline hydrochloride (form a) | 194–196 (ethyl acetate) |
| 4-[(N-Carbo-sec-butoxy-N-phenyl)-amino]-1-[3-(4-fluorobenzoyl)-propyl]-trans-decahydroquinoline hydrochloride (form a) | 178–180 (ethyl acetate) |
| 4-[(N-Carbo-n-butoxy-N-phenyl)-amino]-1-[3-(4-fluorobenzoyl)-propyl]-1-trans-decahydroquinoline hydrochloride (form a) | 181–183 (ethyl acetate) |
| 4-[(N-2-methoxy-carbethoxy-N-phenyl)-amino]-1-[3-(4-fluorobenzoyl)-propyl]-trans-decahydroquinoline hydrochloride (form a) | 159–161 (ethyl acetate) |
| 4-[(N-carbethoxy-N-phenyl)-amino]-1-phenethyl-trans-decahydroquinoline hydrochloride (form a) | 191–193 (ethyl acetate/methanol) |

EXAMPLE 8

Soft-gelatin capsules containing the following ingredients were prepared in accordance with well-known pharmaceutical techniques:

| Ingredients | Weight (1) | (2) |
|---|---|---|
| 4-[(N-phenyl-N-acetyl)-amino]-1-[3-(4-fluorobenzoyl)-propyl]-trans-decahydroquinoline hydrochloride | 25 mg. | 50 mg. |
| Corn-starch | 194.3 mg. | 259.5 mg. |
| Colloidal-silica | 0.7 mg. | 0.5 mg. |
| | 225 mg. | 260 mg. |

EXAMPLE 9

An injectable solution containing the following ingredients was prepared in accordance with well-known pharmaceutical techniques:

| Ingredients | | Weight |
|---|---|---|
| 4-[(N-phenyl-N-acetyl)-amino]-1-[3-(4-fluorobenzoyl)-propyl]-trans-decahydroquinoline hydrochloride | | 60 mg. |
| sorbitol | | 187 mg. |
| water | q.s. | 5 ml. |

I claim:

1. Compounds of the formula:

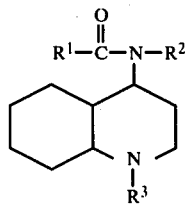

and the pharmaceutically acceptable acid addition salts thereof, wherein $R^1$ represents a branched- or straight-chain alkyl group or alkoxy group of from 1 to 4 carbon atoms, a phenyl or pyridyl group; $R^2$ represents a branched- or straight-chain alkyl group of from 1 to 4 carbon atoms, phenyl, methylphenyl, methoxyphenyl, naphthyl, benzyl, phenethyl, cinnamyl, phenylpropyl or cyclohexyl; and $R^3$ represents a group of the formula:

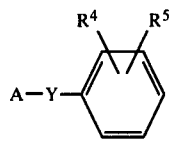

wherein A represents a branched- or straight-chain alkylene group of one to four carbon atoms, inclusive; Y represents an oxygen atom, a carbonyl or carbonyl-hydroxyimino group; $R^4$ and $R^5$, which are identical or different, each represent hydrogen, fluorine, chlorine or bromine, or methyl, methoxy or acetyl.

2. 4-[(N-Phenyl-N-acetyl)-amino]-1-[3-(4-fluorobenzoyl)-propyl]-trans-decahydroquinoline and its pharmaceutically acceptable acid addition salts.

3. 4-[(N-Phenyl-N-carbethoxy)-amino]-1-[3-(4-fluorobenzoyl)-propyl]-trans-decahydroquinoline and its pharmaceutically acid addition salts.

4. A compound as defined by claim 1 wherein $R^1$ is alkyl of 1 to 4 carbon atoms, $R^2$ is phenyl and $R^3$ is fluorobenzoylpropyl.

5. A hydrochloride of the decahydroquinoline compound of claim 2.

6. The hydrochloride of the decahydroquinoline compound of claim 2 which has a melting point of 168°–170° C.

7. The hydrochloride of the decahydroquinoline compound of claim 2 which has a melting point of 188°–190° C.

8. A pharmaceutical analgesic or antihypertensive composition in dosage unit form containing as essential active principle 25 to 60 mg of a compound or a pharmaceutically acceptable acid addition salt thereof as claimed in claim 1 in association with a pharmaceutical carrier or excipient therefor.

9. A pharmaceutical analgesic or antihypertensive composition containing as essential active principle 4-[(N-phenyl-N-acetyl)-amino]-1-[3-(4-fluorobenzoyl)-propyl]-trans-decahydroquinoline or a pharmaceutically acceptable acid addition salt thereof in association with a pharmaceutical carrier or excipient therefor.

10. A pharmaceutical analgesic or antihypertensive composition containing as essential active principle 4-[(N-phenyl-N-carbethoxy)-amino-]-1-[3-(4-fluorobenzoyl)-propyl]-trans-decahydroquinoline or a pharmaceutically acceptable acid addition salt thereof in association with a pharmaceutical carrier or excipient therefor.

11. A composition as claimed in claim 9 in a dosage unit form suitable for oral administration.

12. A composition as claimed in claim 9 in a dosage unit form suitable for administration by injection.

13. A method of treating pain in a mammal in need of such treatment, said method consisting in systemically administering to the said mammal 25 to 60 mg of at least one compound as defind by claim 1 or a pharmaceutically acceptable acid addition salt thereof.

14. A method of treating pathological disorders of arterial pressure characterized by high blood pressure in a mammal in need of such treatment, said method consisting in systemically administering to the said mammal 25 to 60 mg of at least one compound as defined by claim 1 or a pharmaceutically acceptable acid addition salt thereof.

* * * * *